(12) United States Patent
Kasameyer et al.

(10) Patent No.: US 6,584,831 B1
(45) Date of Patent: Jul. 1, 2003

(54) FAST-RECOVERY VISCOMETER

(75) Inventors: Robert E. Kasameyer, Cohasset, MA (US); Wayne Warren, Lexington, MA (US)

(73) Assignee: Cambridge Applied Systems, Inc., Medford, MA (US)

( * ) Notice: Subject to any disclaimer, the term of this patent is extended or adjusted under 35 U.S.C. 154(b) by 0 days.

(21) Appl. No.: 10/038,491

(22) Filed: Dec. 21, 2001

(51) Int. Cl.⁷ ............................................. G01N 11/10
(52) U.S. Cl. .................................................. 73/54.23
(58) Field of Search ........................... 73/54.01, 54.23, 73/54.38

(56) References Cited

U.S. PATENT DOCUMENTS

| | | | | |
|---|---|---|---|---|
| 2,957,338 A | * | 10/1960 | Kennedy et al. | 73/54.23 |
| 3,073,151 A | * | 1/1963 | Fann | 73/54.23 |
| 3,227,916 A | * | 1/1966 | Deming | 315/5.48 |
| 3,677,070 A | * | 7/1972 | Norcross | 73/54.21 |
| 4,627,272 A | * | 12/1986 | Wright | 73/54.23 |
| 4,864,849 A | | 9/1989 | Wright | |
| 5,025,656 A | | 6/1991 | Wright | |

FOREIGN PATENT DOCUMENTS

JP 361161436 A * 7/1986 ................. 73/54.01

* cited by examiner

Primary Examiner—Robert Raevis
Assistant Examiner—Michael Cygan
(74) Attorney, Agent, or Firm—Cesari and McKenna, LLP

(57) ABSTRACT

Electrical current driven through one or the other of two coils (20 and 22) draws a ferromagnetic bob (28) along a chamber (26) containing a liquid whose viscosity is to be measured. The current that flows through the coil includes an AC component, and the resultant magnetic field causes in the other coil an AC voltage whose magnitude depends on the bob's position. A position detector (38, 40) monitors the electromotive force thus induced and concludes that the ferromagnetic bob has reached a predetermined end-of-travel position when the magnitude of the electromotive force has fallen to a predetermined fraction the maximum value that it had attained during the stroke, and a coil driver (36, 38) switches current drive from one coil to the other so as to begin driving the bob in the opposite direction. If the position detector fails to detect the bob's reaching the end-of-travel position within a predetermined timeout interval, the coil driver reverses coil drive despite the absence of such detection. The predetermined timeout interval's duration is ordinarily determined as a function of the bob-stroke duration that recent valid end-of-travel detections have defined. When the first timeout occurs, though, the time-out-interval duration is the same, relatively short value for each of the plurality of strokes in a clean-out period, after which the timeout-interval duration is immediately increased to a relatively high value.

14 Claims, 4 Drawing Sheets

US 6,584,831 B1

FAST-RECOVERY VISCOMETER

BACKGROUND OF THE INVENTION

1. Field of the Invention

The present invention concerns viscometers. It is directed particularly to the type that drives a bob in alternating directions through the liquid to be measured and infers the liquid's viscosity from the duration of a bob stroke.

2. Background Information

U.S. Pat. No. 4,864,849 to Hubert A. Wright, which is hereby incorporated by reference, describes a type of viscometer that is particularly simple mechanically. A bob containing ferromagnetic material is disposed in a channel that a liquid to be measured can enter. A coil is so positioned that the magnetic field caused when current flows through it tends to draw the bob in one direction along the channel. A second coil is so positioned as to draw the bob along the channel in the opposite direction. Driving first one coil and then the other applies an alternating magnetic force to the ferromagnetic-material-including bob, and the viscosity of the liquid through which the bob is thus driven can be inferred from a speed at which it travels through the liquid in response to these magnetic forces.

This use of coils to drive the bob is advantageous because the same coils can also be used for the bob-position sensing that inferring viscosity from bob speed requires. The Wright patent mentioned above describes a convenient approach to using the coils for such sensing. A small AC signal is superimposed on the DC level used to drive the coil that attracts the bob, and the magnetic-field component resulting from the driven coil's AC current causes an AC voltage in the non-driven coil. The non-driven coil is coupled to a filter, which, among other things, increases the system's signal-to-noise ratio. Because the bob includes ferromagnetic material, coil inductance varies with bob position. In the Wright arrangement, the variation is such that the resultant filter-output amplitude increases to a maximum when the position of the bob's ferromagnetic material is approximately symmetrical with respect to the coils, and the amplitude decreases thereafter. The Wright arrangement concludes that the bob has reached the end of its travel when that output's magnitude falls to some predetermined percentage of the maximum that it had attained during the bob stroke. The current drive is then switched from one coil to the other, and the liquid's viscosity is inferred from the time that elapses between end-of-travel detections.

The approach that the Wright patent describes is quite effective, but it has to include provisions that compensate for the effects of delays that result from the need to enhance the system's signal-to-noise ratio by filtering the non-driven coil's output. In a given installation, the viscometer may be intended for use in measuring the viscosity of a relatively viscous liquid, but that liquid's flow through a conduit that the viscometer monitors may be interrupted from time to time by flow of very-low-viscosity liquid. An example occurs in printing-industry installations when an ink-color change takes place and a low-viscosity solvent is used to flush the previous ink color out of the ink lines. The bob travel through the low-viscosity solvent can be too fast that for the detector's filter to follow variations in the non-driven coil's output with any precision. As a result, the filter output does not vary enough to meet the criterion that the system employs to recognize the bob's having reached its predetermined end-of-travel position. The system would therefore fail to switch coil drive in the absence of some contrary provision.

Systems that have employed the Wright approach have therefore included provisions for switching coil drive if the system fails to detect the end-of-travel position within a timeout period whose duration exceeds a stroke duration corresponding to the highest expected viscosity. But suppose that the stroke duration corresponding to the highest viscosity intended to be measured is a full minute. That means that system flushing with a very-low-viscosity solvent would cause a delay of at least a minute before the viscosity of a subsequent, higher-viscosity liquid can be measured.

To reduce this delay, some users have made the timeout-interval duration adjustable, setting it to the sum of some safety margin and the most-recent valid stroke-duration measurement. When the unit times out, they gradually increase the timeout duration until there is a valid end-of-stroke detection before the timeout period ends, presumably because the next, higher-viscosity fluid has begun to flow. When the viscosity of the previous liquid is significantly less than the high end of the intended viscosity range, the shortened timeout period results in less delay.

SUMMARY OF THE INVENTION

We have developed a way reducing the delay even further. In accordance with our invention, the timeout-interval duration that prevails after a timeout has occurred is kept constant through subsequent cycles until a predetermined time period has elapsed, at least if no valid detection occurs in the interim. When that timeout period ends, the timeout-interval duration will typically be increased immediately to a high value.

We have recognized that such an approach has the potential to make the viscometer respond more quickly to transients of the type mentioned above. Timeouts usually are the result of the viscometer's encountering a solvent or some other low-viscosity liquid, as was mentioned above, and, in most environments, the approximate duration of the solvent's flow is known ahead of time. The predetermined time period for which the timeout-interval duration is kept constant will usually be chosen to approximate the expected time of solvent flow, so a valid measurement can usually be based on the first stroke after the timeout interval is raised again. And, if the constant timeout-interval duration is relatively low, the resultant rapid bob reciprocation fills the viscometer's bob chamber more rapidly with the next, higher-viscosity liquid that the viscometer can measure.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
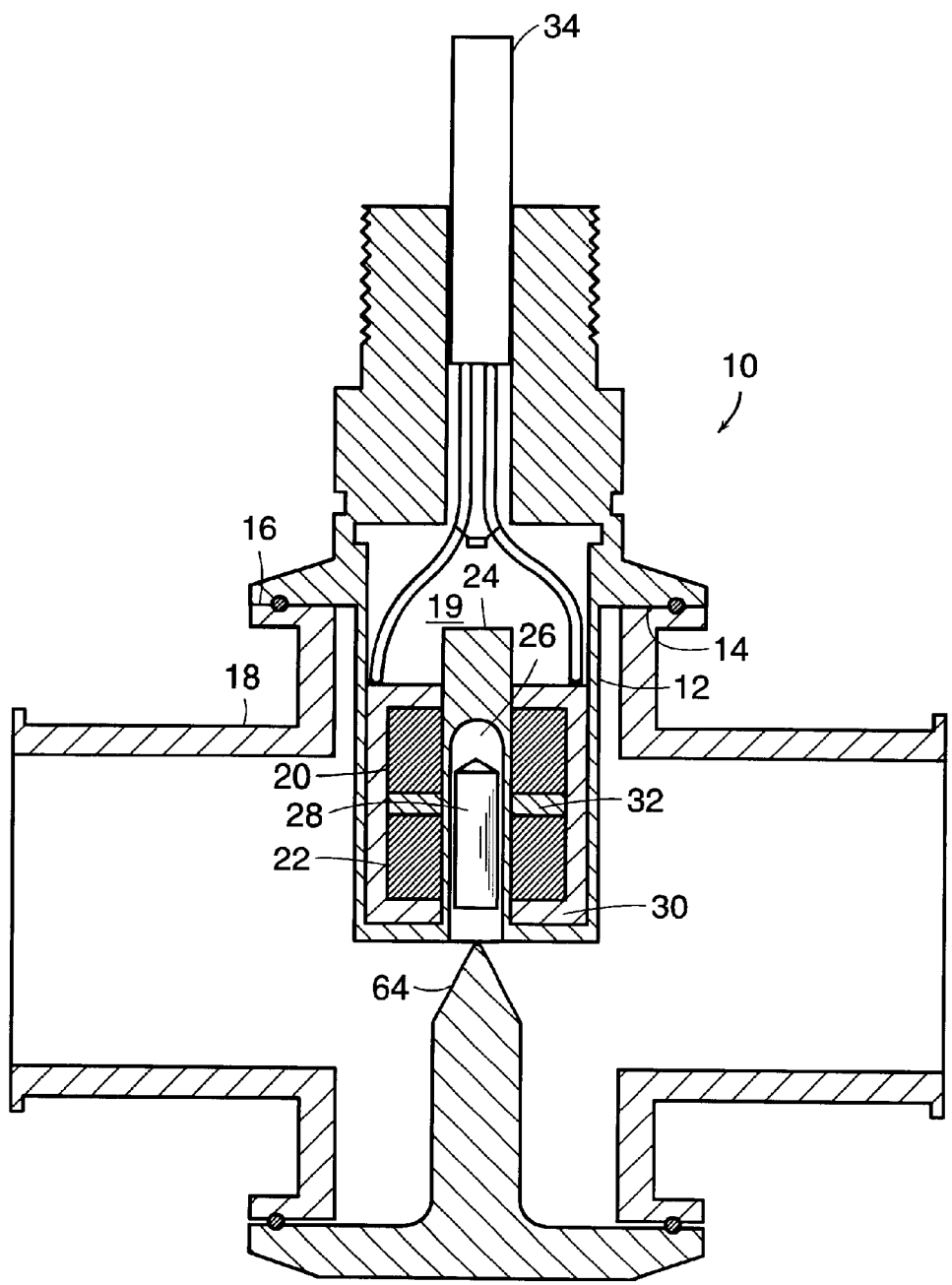
FIG. 1 is a cross-sectional view of the mechanical part of a viscometer that employs the present invention's teachings.

FIG. 1 depicts in cross section the mechanical part 10 of a viscometer that embodies the present invention's teachings. A generally cylindrical shell 12 forms a flange 14 that mates with a joint flange 16 that a pipe 18 forms. The liquid whose viscosity is to be measured flows in the pipe.

The shell forms an interior chamber 19 in which two coils 20 and 22 are mounted. The coils are coaxial with a generally cylindrical bob guide 24 that extends through the coils' central voids and forms a bob chamber 26 in which a bob 28 is slidably disposed. The bob chamber contains liquid from the pipe, and the liquid's viscosity can be inferred from the speed at which a given force causes the bob to move through the liquid.

Surrounding the coils is a coil housing 30 that is generally cylindrical but has disk-shaped ends forming openings though which the bob guide 24 extends. Unlike the shell 12, the coil housing 30 is made of ferromagnetic material, as is a disk-shaped divider 32 disposed between the coils 20 and 22. The bob, too, includes ferromagnetic material, so it can be made to reciprocate by driving the two coils alternately with current from a cable 34. The bob 28 can be made solely of ferromagnetic material, or it can, say, include a non-ferromagnetic, corrosion-resistant envelope enclosing ferromagnetic material.

Since the bob includes ferromagnetic material, its movement changes coil inductance, and bob position can therefore be inferred from measurements of inductance-dependent quantities. Although the illustrated embodiment measures the amplitude of the voltage signal that magnetic coupling from the driven coil causes in the non-driven coil, and although this quantity is a particular function of both mutual and self inductance, quantities that are different functions of position-dependent coil inductance can be measured instead. By thus measuring the time that the bob takes to move between two positions, the viscometer determines the viscosity of the liquid in the bob chamber.

As the bob 28 reciprocates, it tends to refresh the contents of the bob chamber 26. Specifically, the bob's movement away from the bob chamber entrance tends to drive fluid from the bob chamber into the pipe, and the bob's movement toward the entrance tends to draw fluid from the pipe into the bob chamber.

Figure 2:
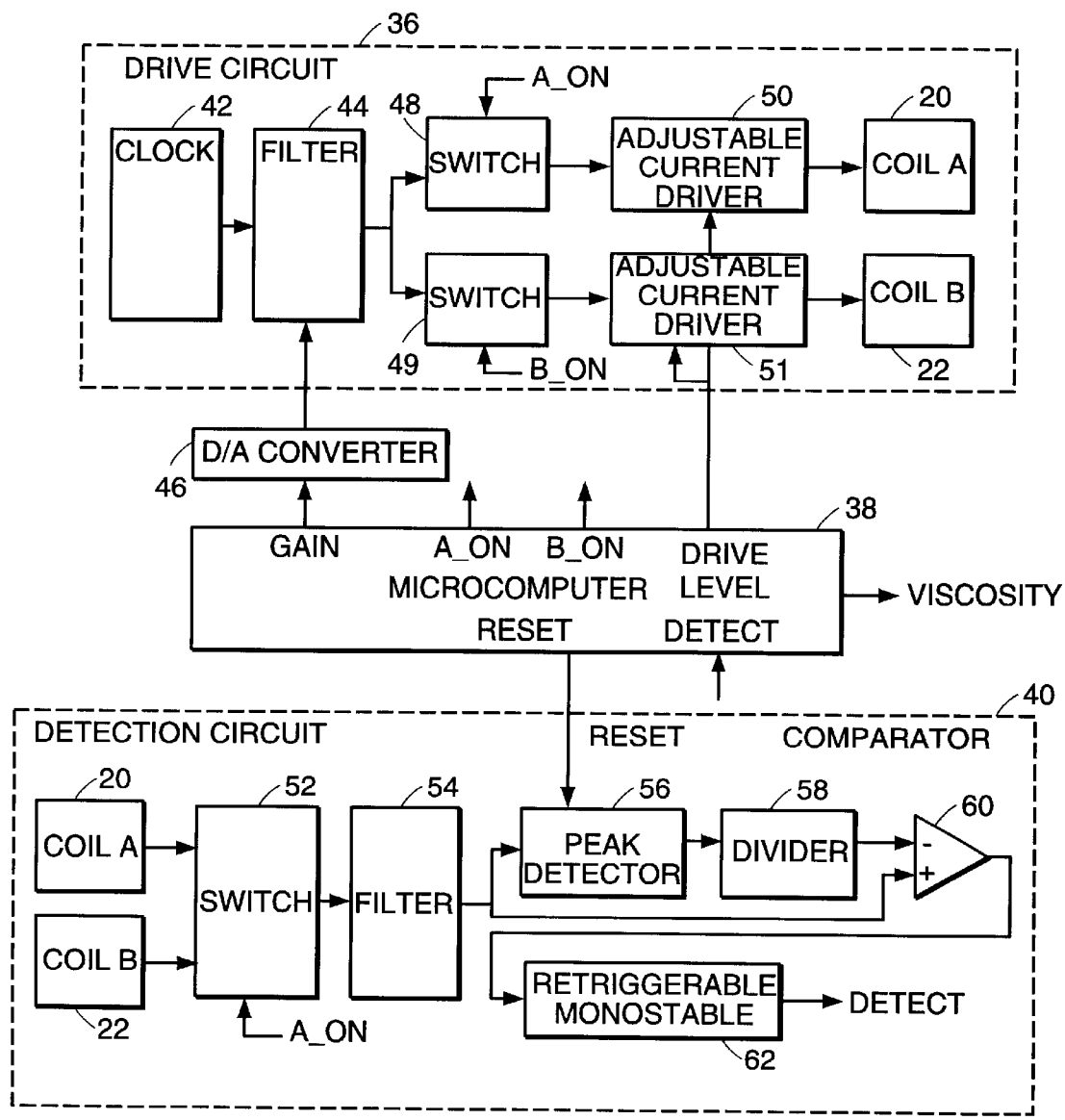
FIG. 2 is a block diagram of the viscometer's electronics.

FIG. 2 depicts circuitry to which cable 34 of FIG. 1 connects the viscometer's mechanical part. A drive circuit 36 cooperates with a microcomputer 38 to act as a coil driver that alternately drives coils 20 and 22. A_ON and $B_{13}$ ON signals generated by a microcomputer 38 indicate which coil the drive circuit is to drive. In determining which coil to select, the microcomputer 38 relies on a DETECT signal, which detection circuitry 40 generates to indicate when the bob 26 has reached either of two predetermined positions in its travel. As will be explained in more detail presently, the detection circuitry cooperates with the microcomputer 38 to act as a position detector that monitors the AC signals on coils 20 and 22 for this purpose. The microcomputer 38 also uses the time between successive DETECT signals in determining the liquid's viscosity: it bases the value of a VISCOSITY output that it generates on bob 28's round-trip travel time.

The drive circuitry 36 includes a clock 42 whose output is a square wave having a DC level. A low-pass filter 44 removes the higher-frequency components from the square wave to produce an approximately sinusoidal AC component. In the filter's output, this AC component is superimposed on a DC level set by a digital-to-analog converter 46's output. The microcomputer 38 uses the digital-to-analog converter 46's input signal, GAIN, to control that DC component. The DC component provides the coils' main drive current. The current that the AC component causes to flow in one coil causes an AC voltage whose amplitude is a function of position-dependent inductances. The detection circuit 40 monitors that voltage.

Switches 48 and 49 respond to the A_ON and B_ON signals by forwarding filter 44's output selectively to respective driver circuits 50 and 51, which respectively drive coils 20 and 22. The drivers 50 and 51 are high-output-impedance circuits: they produce currents whose magnitudes are determined by drive-level signals from the microcomputer and are not greatly affected by coil-impedance changes. The A_ON and B_ON signals are so timed that the coils are driven alternately: when coil 20 is being driven, coil 22 is not, and vice versa.

Taking its state from the value of the A_ON signal, the detection circuit 40's switch 52 forwards the non-driven coil's voltage to a band-pass filter 54. That filter's output amplitude depends on bob position. For one thing, the magnetic coupling between the coils depends on that position. More important in the illustrated embodiment, that filter's center frequency depends on the inductance of the coil 20 or 22 to which the switch 52 connects it. That in turn depends on bob position in such a manner that the center frequency equals clock 42's fixed fundamental frequency, i.e., the excitation frequency, when the bob is in the middle of its travel. Filter 54 feeds its output to the remainder of the detection circuitry 40. As was mentioned above, that circuit's purpose is to determine when the bob 26 has reached a predetermined point in each stroke.

For the sake of discussion, we will assume that the viscometer's mechanical part 10 is oriented vertically, as FIG. 1 indicates, although orientation is largely irrelevant. When the bob 26 begins its top-to-bottom stroke, most of the bob 28's ferromagnetic material is initially disposed between the coil housing 30's top end and ferromagnetic divider 32, with the result that coil 20's inductance is relatively low. As the bob moves down, that coil's inductance falls, moving the filter's center frequency closer to the excitation frequency until the bob's ferromagnetic material is positioned more or less symmetrically with respect to the coils. As the filter's center frequency thus approaches the excitation frequency, the filter output's amplitude increases. After that, further downward travel places most of the bob's ferromagnetic material between the ferromagnetic divider 32 and the coil housing's lower end. The resultant further reduction in coil 20's inductance now moves the filter's center frequency past the excitation frequency, so the filter output's amplitude falls below the mid-stroke peak. By determining when the amplitude has fallen to a predetermined percentage of its peak value, the detection circuitry determines when the bob 26 has reached a predetermined position toward the end of its downward travel.

Specifically, the filter 54 applies its output to a peak detector 56. The peak detector retains as its output the highest instantaneous voltage that it has received from filter 54 since a transition in the microcomputer's RESET output last reset it, at the beginning of the stroke. From that peak voltage, a voltage divider 58 produces an output that is, say, 90% of the peak detector's output. A comparator 60 subtracts this 90%-peak signal from the filter output and thereby produces a square wave so long as the peaks of the filter output exceed 90% of their highest previous level during the current stroke. That is, the comparator output takes the form of a square wave while the amplitude increases with downward travel, and it continues to be a square wave until the amplitude falls back to 90% of the peak. At that point, the square wave ceases, indicating that the predetermined position has been reached.

The comparator sends its output to a one-shot circuit, a retriggerable monostable multivibrator 62. The one-shot's purpose is to generate a high output so long as the square wave is present: its output must stay high between triggerings by the comparator output's low-to-high transitions, but it must eventually go low when the square wave ceases. So the one-shot 62's characteristic delay is greater than the clock period and thus greater than the period of comparator 60's square-wave output. Preferably, that characteristic delay is actually several clock periods, because this makes the detection circuitry relatively immune to noise that might suppress one of comparator 60's output pulses. When the bob 26 reaches the predetermined position and the comparator 60's output square wave therefore ceases, the one-shot 62 stops being triggered, and its output, the DETECT signal, goes low after the one-shot's characteristic delay.

Normally, the microcomputer 38 treats this high-to-low DETECT-signal transition as an end-of-stroke indication. In response to this indication, it reads and resets a stroke-duration counter that it has incremented periodically since the last such resetting, it changes the states of switches 48 and 49 to start driving the bob 26 in the opposite direction, it operates switch 52 to the state in which the detection circuit 40 receives the voltage of the coil from which coil drive has just been removed, and it resets the peak detector 56. It then adds the just-read stroke duration to the previous stroke's duration and computes from the result the viscosity of the liquid through which the bob traveled, and it generates a VISCOSITY output, which represents the value thereby computed.

There are occasions when the microcomputer changes switch states and thereby begins another stroke without waiting for the DETECT-signal transition. To understand why, remember that the filter 54 must have a bandwidth narrow enough to provide the required degree of noise suppression. This means that it can respond to input changes only slowly. A consequence of its slowness to respond is that, if the bob travels too fast, the filter output's peak will not exceed its other values by enough for the output of divider 88 ever to exceed the filter output's instantaneous peaks. So comparator 60's output will keep on triggering monostable multivibrator 62 even after the bob reaches the end of its travel, and the DETECT signal will not make the high-to-low transition that the microcomputer treats as the end-of-travel indication.

In the absence of a provision to deal with this, the same coil—say, coil 22—would continue to be driven indefinitely, although a stop 64 (FIG. 1) provided for that purpose would end bob travel. So bob time-out routines have been employed to deal with this possibility. If the stroke-duration counter reaches a predetermined timeout value, viscosity is not computed from it, and the coil drive is switched even though the circuit has not detected that the bob has reached the end of its travel. This prevents the viscometer system from "hanging up."

A way of employing such a time-out routine is to make the time-out duration some fixed value equal to, say, 20% higher than the highest expected bob-stroke duration. According to the present invention, though, that timeout duration varies in accordance with previously measured stroke durations, as will now be explained.

Figure 3A:
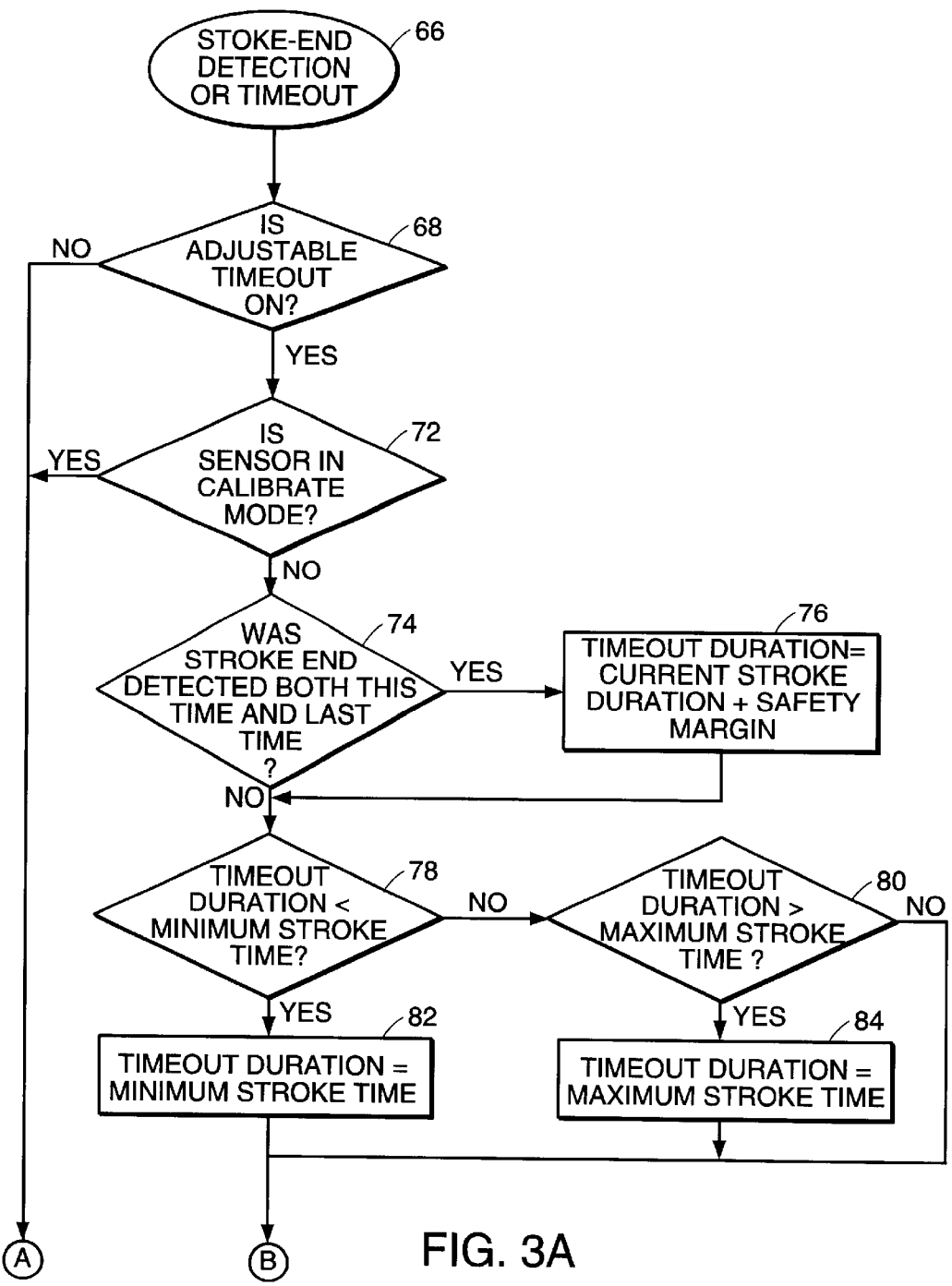
FIGS. 3A and 3B together form a flow chart depicting the manner in which the viscometer adjusts its timeout period.
Figure 3B:
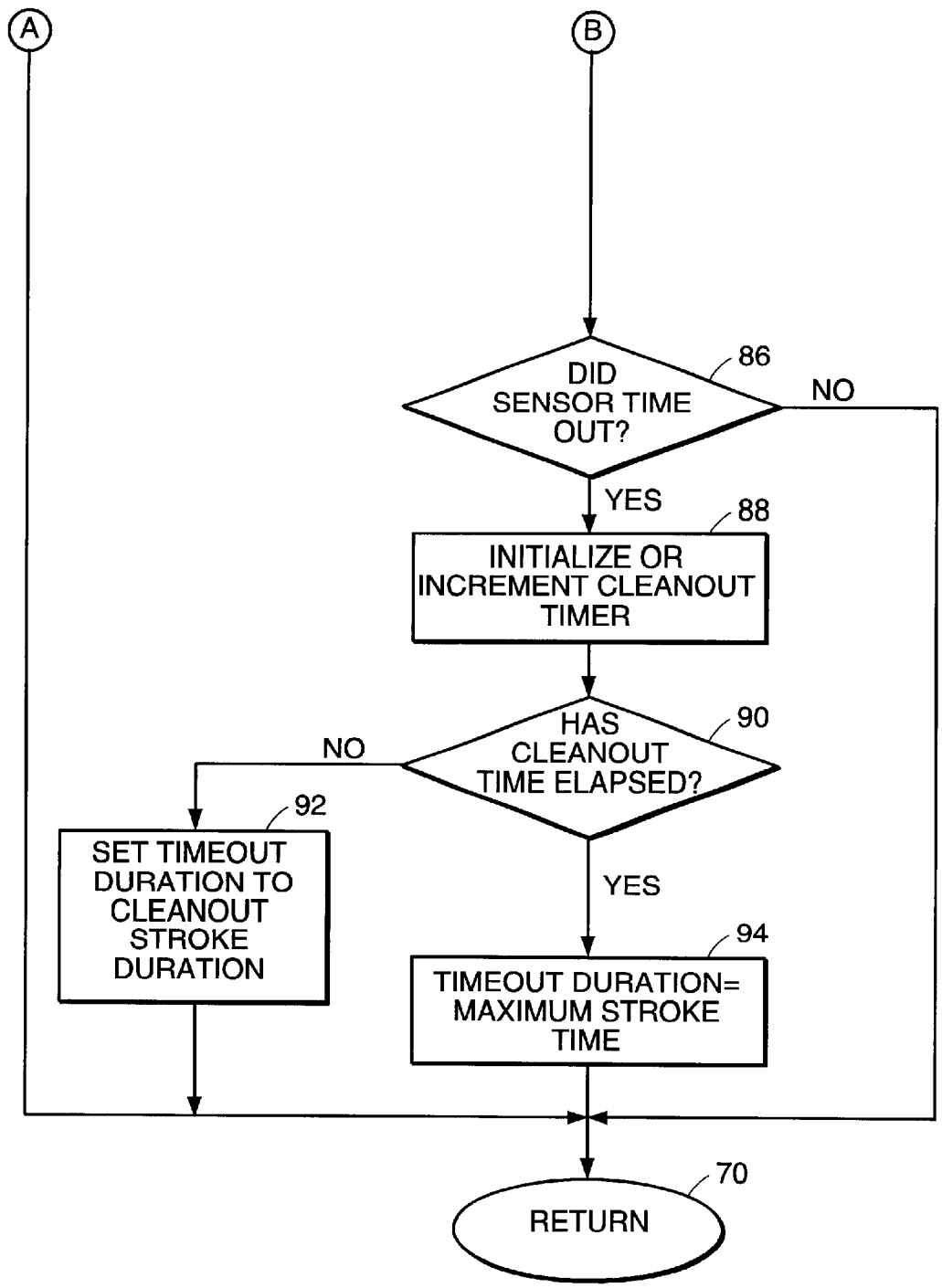

FIGS. 3A and 3B (together, "FIG. 3") form a flow chart of one of typically several routines that the microcomputer 38 enters at the end of a bob stroke. As was just explained, the circuitry of FIG. 2 ordinarily considers a stroke to end when detection of the bob's passing through one of the predetermined positions causes the DETECT signal to make a high-to-low transition. Block 66 represents the occurrence of this transition or the end of the timeout interval, and such an event is the trigger for the microcomputer 38 to perform the remainder of FIG. 3's operations, typically after it performs some other similarly triggered tasks.

As will presently be explained in more detail, the timeout interval's duration is variable in accordance with the present invention, but systems that employ the present invention's teachings may additionally provide a mode in which the timeout duration does not vary, and block 68 represents determining whether the system is in the mode in which its timeout duration is indeed variable. If not, the system simply skips the remainder of FIG. 3's operations, as block 70 indicates.

Also, most such systems will provide a calibration mode, in which the present invention's teachings would not be employed, either. Block 72 represents therefore determining whether the system is in that mode. If not, the system employs the present invention's teachings of making the timeout interval's duration depend on recent stroke-interval durations. Although embodiments of the present invention may employ any one of a wide variety of relationships between recent stroke-interval durations and timeout duration, the illustrated embodiment employs a timeout duration that simply equals the sum of the just-measured stroke duration and a safety margin, but only if the resultant timeout duration is within predetermined limits and only of the reliability of the most-recent stroke-interval duration's measurement is indicated by the fact the end-of-travel detections occurred before the end of the timeout interval for both of the previous two bob strokes.

Block 74 represents imposing the latter condition: it is only if the condition is met that the routine performs block 76's step of making the timeout duration equal to the last measured stroke duration plus some safety margin. Blocks 78, 80, 82, and 84 represent keeping the timeout duration within predetermined limits.

If a valid end-of-travel detection did indeed occur, then the determination made in the step represented by block 86 is negative: the timeout interval did not expire without a valid detection. In that case, the timeout interval has been set appropriately, and the microcomputer ends its performance of the FIG. 3 routine, as block 70 indicates. If that routine was instead entered as a result of the timeout interval's having ended before a valid end-of-travel detection, on the other hand, the illustrated embodiment begins a clean-out operation, which will continue for several strokes.

To understand why the illustrated embodiment performs the clean-out operation, it helps first to consider the likely reasons why the timeout interval has elapsed. One possible reason is that the liquid being measured is so viscous that the stroke duration exceeded the timeout-interval maximum imposed in FIG. 3's block 84. In most instances, though, that maximum is set to a value greater then any viscosity likely to be encountered in the viscometer's environment, so this is not the normal reason why the timeout interval will have elapsed.

More typically, the timeout interval has elapsed because the viscosity has fallen below the normal measurement range. Such a situation may arise in printing environments, for example. The liquid whose viscosity is to be measured may be a relatively viscous ink, but the lines carrying the ink may be flushed out from time to time with a solvent whose viscosity is well below the expected measurement range. When the lines thus contain solvent, the bob moves too fast for the detection circuitry, and a valid end-of-travel detection does not occur. When this happens, it is desirable for the bob to reciprocate rapidly for some time. The rapid reciprocation enables the solvent to remove ink of the previous color from the bob chamber quickly. Then, when the new ink begins to flow, it rapidly draws ink of the new color into that chamber.

In the absence of the present invention's timeout-duration adjustment, though, the time that would elapse before the system reacts to the solvent flow by timing out would be relatively long; it would exceed the length of time that a valid stroke would take for a liquid whose viscosity is at the high end of the range. In contrast, the present invention enables the system to respond more quickly whenever the previous liquid's viscosity was not at the high end of the range.

It responds by entering a period of rapid reciprocation. To this end, the routine of FIG. 3 includes a step, represented by block 88, of starting a clean-out timer, which is intended to count up to a value representing the intended duration of a clean-out period, during which the bob reciprocates rapidly to refresh the bob-chamber contents. That clean-out duration will depend on the particular environment in which the viscometer is employed. In the case of the multi-color-ink environment just mentioned, the duration may approximately equal the expected length of time required for solvent to flush the lines and for flow of a new-color ink to begin. Such an interval will span many bob reciprocations, so the result of the block-90 test will be negative during an execution of the FIG. 3 routine in which the block-88 operation initializes the clean-out timer. As block-92 indicates, therefore, the timeout duration that will be employed for the next stroke is a relatively short, cleanout-stroke duration. As block 70 indicates, the FIG. 3 routine returns each time after thus setting the timeout duration to the clean-out stroke duration, and the system awaits the end of the next stroke.

The clean-out-stroke duration is so short that the stroke timer next times out before any valid detection can occur. The routine will therefore be entered the next time as a result of a timeout rather than as a result of a valid end-of-stroke detection. So there will again be a positive result when the routine reaches the step that block 86 represents. The block-88 and block-92 steps of incrementing the clean-out timer and setting the timeout duration to the short, clean-out-stroke duration will be repeated, so a timeout rather than a valid end-of-stroke detection will again be what causes the routine to be entered the next time.

The timeout-interval duration used in the illustrated embodiment during the clean-out period is a preset value that is independent of events that occur during viscometer operation. But some embodiments may instead give it a value that depends on the duration of one or more previous, valid strokes. Once the clean-out period starts, though, that duration remains the same, constant clean-out-stroke duration.

After a number of clean-out-period strokes, block 88's incrementing the clean-out timer causes it to reach the intended clean-out duration. When that happens, the block-90 test yields a positive result, and the timeout duration, which had been the short, clean-out-stroke duration, is immediately set to the stroke duration corresponding to the high end of the viscosity scale. What that duration is will vary from installation to installation, but it will be relatively long, equal to at least six times the clean-out-stroke duration, and typically considerably longer. In one system in which we have employed a clean-out-stroke duration of two seconds, for example, the timeout duration is immediately increased to thirty-two seconds at the end of the clean-out time.

Now, the clean-out time will have been so set as normally to extend through the solvent-flush interval and into the beginning of the new ink's flow. And the rapid reciprocation that resulted from the short timeout duration will rapidly have filled the bob chamber with the new ink. The fluid in the bob chamber will therefore cause the bob to travel slowly enough to permit a valid end-of-stroke detection. So such a detection is what will cause the routine to be entered the next time, and the viscometer will be able to make a valid measurement of the new ink's viscosity.

In short, the rapid reciprocation that in accordance with the present invention occurs during the clean-out interval enables the viscometer to respond rapidly to the ink change, and the change in timeout duration from the short, clean-out-stroke duration to the maximum stroke duration enables that first stroke after the clean-out interval ordinarily to be used in making a valid viscosity measurement. So the present invention enables the viscometer to respond more quickly than conventional arrangements and therefore constitutes a significant advance in the art.

What is claimed is:

1. A viscometer system including:
   A) a bob;
   B) bob guide that guides the bob along a bob path in which a fluid whose viscosity is to be measured can be disposed;
   C) first and second coils so positioned with respect to the path that current flowing through them produces respective magnetic fields that tend to drive the bob along the bob path in respective opposite directions;
   D) a position detector responsive to the coils' inductance to produce a detector signal that indicates when the bob has reached end-of-travel positions if the bob speed does not exceed a bob-speed maximum;
   E) a coil driver that:
      i) alternately drives the first and second coils in respective drive strokes and is responsive to the position detector to switch between the first and second coils upon the earlier of:
         a) the time at which the detector signal indicates when the bob has reached one of the end-of-travel positions; and
         b) the end of a predetermined timeout interval;
      ii), sets the duration of the predetermined timeout interval employed during a drive stroke to a value that it determines as a function of the duration of at least one previous drive stroke; and
      iii) responds to a stroke's first lasting to the end of a timeout interval by keeping the duration of the timeout interval at a fixed, clean-out-stroke value for a clean-out period comprising a plurality of strokes at least if the detector signal does not in the interim indicate that the bob has reached one of the end-of-travel positions;
      iv) sets the duration of the predetermined timeout interval for the first stroke after the clean-out period to a value at least six times the clean-out-stroke value; and
   F) an output generator responsive to the drive strokes' durations to generate a viscosity output representative of the viscosity that the strokes' durations indicate.

2. A viscometer as defined in claim 1 wherein the value to which the coil driver sets the duration of the predetermined timeout interval in at least some instances is the sum of the last stroke duration and a safety-margin value.

3. A viscometer as defined in claim 1 wherein the value to which the coil driver sets the duration of the predetermined timeout interval is the sum of the last stroke duration and a safety-margin value only if that sum falls within predetermined-timeout-value limits.

4. A viscometer as defined in claim 1 wherein the value to which the coil driver sets the duration of the predetermined timeout interval is the sum of the last stroke duration and a safety-margin value only if the detector signal indicated that the bob had reached one of the end-of-travel positions during the previous stroke before the end of the timeout period.

5. A viscometer as defined in claim 4 wherein the value to which the coil driver sets the duration of the predetermined timeout interval is the sum of the last stroke duration and a safety-margin value only if the detector signal indicated that the bob had reached one of the end-of-travel positions, during the stroke before the previous one, before the end of the timeout period.

6. A viscometer as defined in claim 4 wherein the value to which the coil driver sets the duration of the predetermined timeout interval is the sum of the last stroke duration and a safety-margin value only if that sum falls within predetermined timeout-value limits.

7. A viscometer as defined in claim 1 wherein the fixed, clean-out-stroke value is independent of previous stroke durations.

8. A method of measuring viscosity that includes:
  A) providing a bob guide that includes:
    i) a bob;
    ii) bob guide that guides the bob along a bob path in which a fluid whose viscosity is to be measured can be disposed;
    iii) first and second coils so positioned with respect to the path that current flowing through them produces respective magnetic fields that tend to drive the bob along the bob path in respective opposite directions; and
    iv) a position detector responsive to the coils' inductance to produce a detector signal that indicates when the bob has reached end-of-travel positions if the bob speed does not exceed a bob-speed maximum;
  B) alternately driving the first and second coils in respective drive strokes and is responsive to the position detector to switch between the first and second coils upon the earlier of:
    i) the time at which the detector signal indicates when the bob has reached one of the end-of-travel positions; and
    ii) the end of a predetermined timeout interval;
  C) setting the duration of the predetermined timeout interval employed during a drive stroke to a value that it determined as a function of the duration of at least one previous drive stroke;
  D) responding to a stroke's first lasting to the end of a timeout interval by keeping the duration of the timeout interval at a fixed, clean-out-stroke value for a clean-out period comprising a plurality of strokes at least if the detector signal does not in the interim indicate that the bob has reached one of the end-of-travel positions;
  E) setting the duration of the predetermined timeout interval for the first stroke after the clean-out period to a value at least six times the clean-out-stock value; and
  F) in response to the drive strokes' durations, generating a viscosity output representative of the viscosity that the strokes' durations indicate.

9. A method as defined in claim 8 wherein the value to which the duration of the predetermined timeout interval is set in at least some instances is the sum of the last stroke duration and a safety-margin value.

10. A method as defined in claim 8 wherein the value to which the duration of the predetermined timeout interval is set is the sum of the last stroke duration and a safety-margin value only if that sum falls within predetermined timeout-value limits.

11. A method as defined in claim 8 wherein the value to which the duration of the predetermined timeout interval is set is the sum of the last stroke duration and a safety-margin value only if the detector signal indicated that the bob had reached one of the end-of-travel positions during the previous stroke before the end of the timeout period.

12. A method as defined in claim 11 wherein the value to which the duration of the predetermined timeout interval is set is the sum of the last stroke duration and a safety-margin value only if the detector signal indicated that the bob had reached one of the end-of-travel positions, during the stroke before the previous one, before the end of the time-out period.

13. A method as defined in claim 11 wherein the value to which the duration of the predetermined timeout interval is set is the sum of the last stroke duration and a safety-margin value only if that sum falls within predetermined timeout-value limits.

14. A method as defined in claim 8 wherein the fixed, clean-out-stroke value is independent of previous stroke durations.

* * * * *